(12) United States Patent
McGinley et al.

(10) Patent No.: US 11,464,525 B2
(45) Date of Patent: Oct. 11, 2022

(54) CABLE AND ROLLER BONE SAW

(71) Applicant: McGinley Engineered Solutions, LLC, Casper, WY (US)

(72) Inventors: Joseph C. McGinley, Casper, WY (US); Adam M. Johnson, Casper, WY (US)

(73) Assignee: MCGINLEY ENGINEERED SOLUTIONS, LLC, Casper, WY (US)

( * ) Notice: Subject to any disclaimer, the term of this patent is extended or adjusted under 35 U.S.C. 154(b) by 212 days.

(21) Appl. No.: 16/876,609

(22) Filed: May 18, 2020

(65) Prior Publication Data

US 2020/0360029 A1 Nov. 19, 2020

Related U.S. Application Data

(60) Provisional application No. 62/849,524, filed on May 17, 2019.

(51) Int. Cl.
*A61B 17/16* (2006.01)
*A61B 34/00* (2016.01)
*A61B 17/17* (2006.01)

(52) U.S. Cl.
CPC .......... *A61B 17/1637* (2013.01); *A61B 17/17* (2013.01); *A61B 34/71* (2016.02); *A61B 2034/715* (2016.02)

(58) Field of Classification Search
CPC ..... A61B 17/1637; A61B 34/71; A61B 17/17; A61B 2034/715; A61B 17/16; A61B 17/164; A61B 17/1642; A61B 17/1659; A61B 17/1697; A61B 17/14; A61B 17/147
See application file for complete search history.

(56) References Cited

U.S. PATENT DOCUMENTS

| | | | |
|---|---|---|---|
| 9,314,253 B2 * | 4/2016 | Mimran | A61B 17/864 |
| 9,456,829 B2 * | 10/2016 | Saadat | A61B 17/1659 |
| 2005/0216023 A1 * | 9/2005 | Aram | A61B 17/17 606/86 R |
| 2007/0073308 A1 * | 3/2007 | Anderson | A61B 18/203 606/96 |
| 2008/0312658 A1 * | 12/2008 | Namba | A61B 17/147 606/82 |

* cited by examiner

*Primary Examiner* — Kevin T Truong
*Assistant Examiner* — Diana Jones
(74) *Attorney, Agent, or Firm* — Holzer Patel Drennan

(57) ABSTRACT

A surgical saw for use in cutting bone. The saw may include a cutting member that is rotated about a drive pulley, an idler pulley, and first and second guide members. The guide members are in contact with an outer perimeter surface of a bone to be cut. The guide members may be moveable in opposite directions relative to the outer perimeter surface. In turn, the cutting member may be engaged with the bone in response to the movement of the guide members. The guide members may move along the outer perimeter surface of the bone until the cutting member has been moved through an entire cross-section of a bone to separate the bone. The saw may be initially inserted in a bore created in the bone to dispose the idler pulley at an opposite side of the bone as the drive pulley when commencing the cutting operation.

21 Claims, 18 Drawing Sheets

CABLE AND ROLLER BONE SAW

FIELD

The present disclosure relates to orthopedic surgical instruments, and in particular, a saw for cutting through a bone.

BACKGROUND

Bones are often cut or sawed through, entirely or partially, in surgical operations. Such operations are performed using traditional saw instruments, which can come in a variety of configurations. For instance, sagittal saws, circular saws, reciprocating saws, cut-off wheels on a straight spindle grinder tool, or other instruments are used in such operations. Alternatively, traditional hand held straight saw blades might be used to cut through a bone.

In any of these traditional approaches, a significant risk for soft tissue damage exists as each of these approaches rely on a surgeon's skill in manipulating the saw to avoid inadvertent contact with soft tissue surrounding the bone. However, regardless of the skill of the surgeon operating, it may be difficult or impossible to reliably control a saw in all contexts when sawing through a bone. A particular concern relates to the completion of a cut when the saw may experience "plunge" or a rapid acceleration beyond the bone at the completion of the cut. Moreover, to avoid inadvertent soft tissue damage, the bone is often isolated from the soft tissue by manipulating surrounding soft tissue (e.g., retracting or otherwise separating soft tissue from the bone). Manipulation or contact of soft tissue may lead to increased trauma associated with an operation, which may lead to extended healing times and reduces the efficacy of an operation. Accordingly, the need exists for a saw device that may efficiently and reliably cut through a bone while reducing the risk of inadvertent soft tissue damage.

SUMMARY

This Summary is provided to introduce a selection of concepts in a simplified form that is further described below in the Detailed Description. This Summary is not intended to identify key features or essential features of the claimed subject matter, nor is it intended to be used to limit the scope of the claimed subject matter.

The present disclosure generally relates to an orthopedic surgical saw that may be used to cut through or partially through a bone of a patient. Specifically, the saw described herein may reduce the risk to the soft tissue surrounding a bone that is sawed or cut in operation. Rather than traditional approaches to sawing described above that may be susceptible to plunge or other inadvertent contact between the saw and surrounding soft tissue, the present disclosure provides a device that may reduce such potential for soft tissue damage. The saw described herein may utilize a flexible cutting member that traverses about a number of pulleys. A bore may be created in a bone to be cut such that the cutting member and at least one pulley may be disposed through the bore. In turn, the cutting member may extend through the bore of the bone.

With the cutting member extending through the bore of the bone, the cutting member may be activated by rotating the cutting member about the at least one pulley. In turn, as the cutting member contacts the bone (e.g., at the sidewall portions of the bore), the cutting member may cut the bone. In this regard, the cut may occur "inside-out" such that the cutting member contacts a portion of the bone in the bore at an interior portion of the bone. In this regard, the at least one pulley may comprise a moveable or displaceable pulley that directs the cutting member into contact with the bone.

The cutting member may rotate about one or more guide pulleys. The guide pulleys may be moveable to engage the cutting member with the side wall portion of the bore to cause the cutting member to cut the bone. The movement of the one or more guide pulleys may be prescribed or controlled to cause the cutting member to engage the bone to reduce or avoid contact with surrounding soft tissue.

In one embodiment, the guide pulleys may be initially located within the bore and may be moved to contact the bone to be cut along a sidewall of the bore. In this regard, the guide pulleys may be maintained within the cross-sectional envelope of the bone such that the guide pulleys may not extend outside an outer perimeter surface of the bone. In such embodiments, the guide pulleys may be engaged with one or more support arms that allow for movement of the guide pulleys within the cross-sectional envelope of the bone. Such support arms may be moveable (e.g., pivotal) relative to a body member of the saw. Additionally or alternatively, the support arms may be capable of extending or retracting to extend the guide pulley relative to the bone to accomplish a cut.

In an embodiment in which the guide pulleys may be moved internally to the bone, the guide pulleys may at least partially comprise a portion of the cutting member. That is, the guide pulleys or guide assemblies, of which the guide pulleys form a portion, may be provided with cutting features in addition to a flexible cutting member which rotates about the guide pulleys. As such, when the guide pulleys are moved within the cross-sectional envelope of the bone, the guide pulleys may cause the bone to be cut, and the cutting member may cause a portion of the bone extending between two respective pulleys to be cut. Further still, in embodiments in which the guide pulleys are moved within the cross-sectional envelope of the bone, care may be taken to reduce the potential for the cutting member erupting from the outer perimeter surface. The risk of eruption of the guide pulleys and/or cutting member may be mitigated by control of the guide pulleys relative to the bone (e.g., by manipulation or other control of the body member and/or support arms).

Moreover, a collar may also be disposed about the outer perimeter surface of the bone to be cut. The collar may be a metallic, polymer, or other appropriate material that may shield surrounding soft tissue in the instance that an eruption of the guide pulley and/or cutting member occurs. The collar may extend about at least a portion of the outer perimeter surface. In some embodiments, the collar may extend about substantially the entire outer perimeter surface, provided that the collar does not interfere with insertion of the saw into the bore of the bone.

In another embodiment, one or more guide pulleys about which the cutting member traverses may be in contacting engagement with an outer perimeter surface of the bone. These pulleys may comprise a guide member. The guide member may have a bearing portion that maintains contacting engagement with the outer perimeter surface. The guide members may be moved in opposite directions about the outer perimeter surface. In turn, as the cutting member traverses about the pulleys, the cutting member may be urged into the sidewall of the bore in which the saw is disposed. As the guide members may be in contacting engagement with the outer perimeter surface of the bone, the exposure of the cutting member to surrounding soft tissue may be minimized. Furthermore, as the guide members may articulate or otherwise move about the outer perimeter portion, upon completion of the cut, the cutting member may not experience plunge or other rapid acceleration associated with the completion of the cut.

In any of the foregoing embodiments, a first bore may be created in the bone to facilitate disposal of at least a portion of the cutting member in the bore to allow for cutting the interior of the bone at the sidewall of the bone. The bore may extend through the bone from a first side of the bone to an opposite side of the bone. For example, the bore may generally extend through the central portion of the bone (e.g., along the midline of the bone). For generally cylindrical bones, this may correspond to a diameter of the cross-sectional area of the bone. In alternative embodiments, a plurality of bores may be created to facilitate routing of the cutting member relative to the bone. For instance, perpendicular bores may be created to effectively provide quadrants of the bone to be cut by the saw. In this regard, a cutting member may be routed to surround the quadrant and allow for the cutting member to be engaged with the bone in a given quadrant. In turn, the pulleys may be moved to a different quadrant, and the cutting process repeated until the quadrants have been cut. In still other embodiments, bores may be created as chord segments extending relative to the cross-sectional area of a bone. Such bores may extend through the bone and facilitate acceptance of the cutting member in the one or more bores to perform a cutting operation.

Accordingly, the operation of the saw device described herein may reduce the reliance on a surgeon to control a saw device to prevent plunge or other soft tissue damage. Furthermore, as the disruption to the soft tissue surrounding the bone to be cut may be reduced, the associated trauma to surrounding soft tissue may also be reduced, thus improving patient outcomes.

Numerous additional features and advantages of the present disclosure will become apparent to those skilled in the art upon consideration of the embodiment descriptions provided hereinbelow.

DETAILED DESCRIPTION

The following description is not intended to limit the disclosure to the forms disclosed herein. Consequently, variations and modifications commensurate with the following teachings, skill, and knowledge of the relevant art, are within the scope of the present disclosure. The embodiments described herein are further intended to explain modes known of practicing the disclosure and to enable others skilled in the art to utilize the disclosure in such, or other embodiments and with various modifications required by the particular application(s) or use(s) of the present disclosure.

Figure 1:
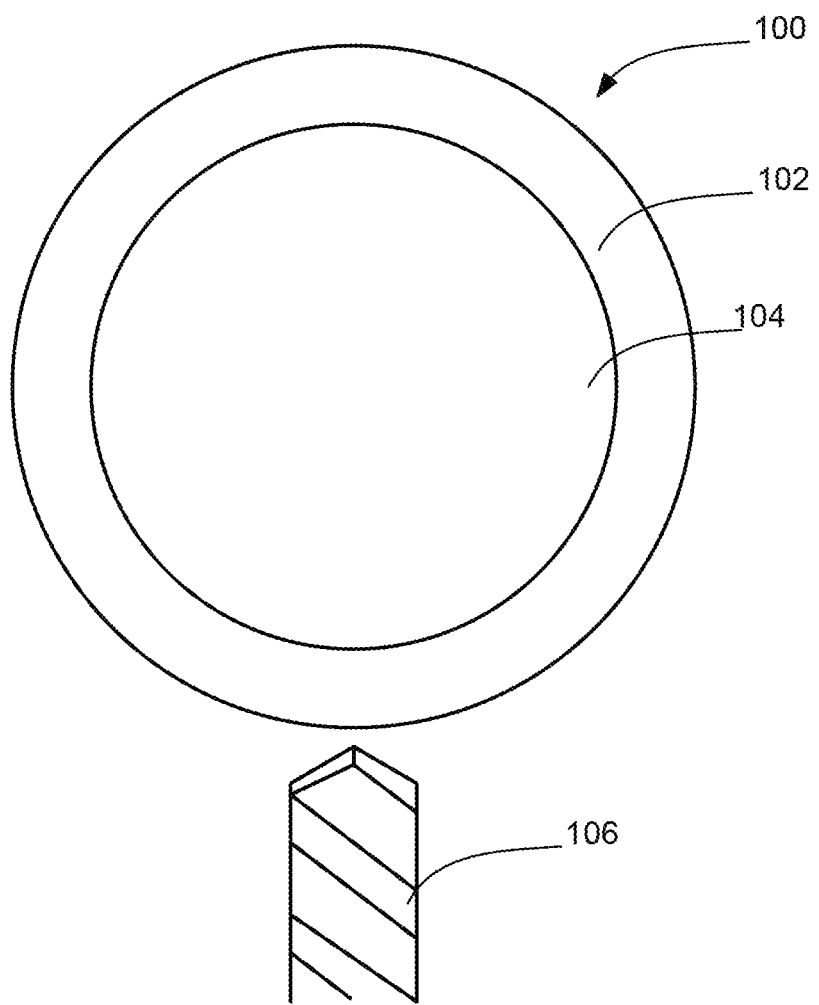
FIG. 1 illustrates a cross-sectional view of a cortical bone having a cortical layer and a medullary portion.

FIG. 1 illustrates a cross-sectional view of a bone 100. The bone 100 may be a cortical bone such that the bone, when viewed in cross-section, includes an outer cortex layer 102 and a medullary portion 104 about which the outer cortex layer 102 extends. As shown in FIG. 1, the bone 100 may have a generally circular cross section indicating that the bone is generally cylindrical, as is the case for many long bones in the body. The bone 100 may include other shapes including irregular shapes without limitation. In this regard, the discussion presented herein references cutting through a generally cylindrical bone. However, the present disclosure is not limited to use in such a context and may be used to cut entirely or partially through a bone of any shape, size, or configuration.

Figure 2:
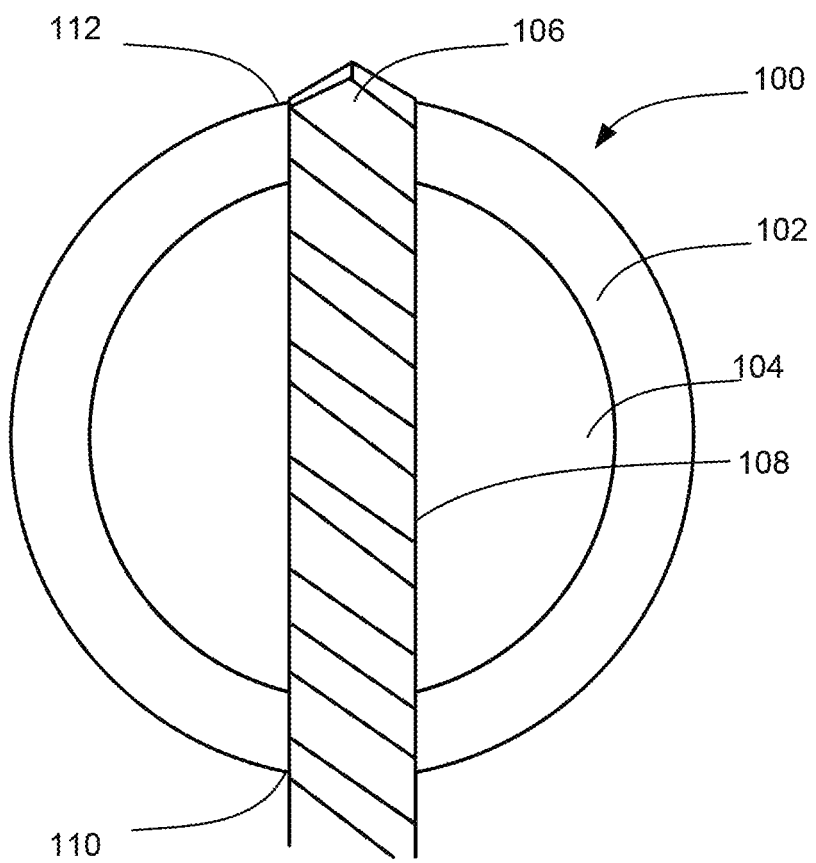
FIG. 2 illustrates the bone of FIG. 1 in which a drill is used to create a bore extending through the bone according to an embodiment of the present disclosure.

FIG. 1 also shows a drill bit 106, which with further reference to FIG. 2, may be advanced through the bone 100 (i.e., through the outer cortex layer 102 and medullary portion 104) to create a bore 108 in the bone 100. The bore 108 may extend entirely through the bone 100 from a first side 110 of the bone to a second side 112 of the bone opposite the first side 110. The drill bit 106 may be engaged with a surgical drill to create the bore. In one example, a drill having a measurement system to measure the length of the bore and/or to arrest the drill once the drill bit 106 exits the bone 100 at the second side 112 may be used such as that described in U.S. Pat. No. 9,358,016, the entirety of which is incorporated by reference herein.

Figure 3:
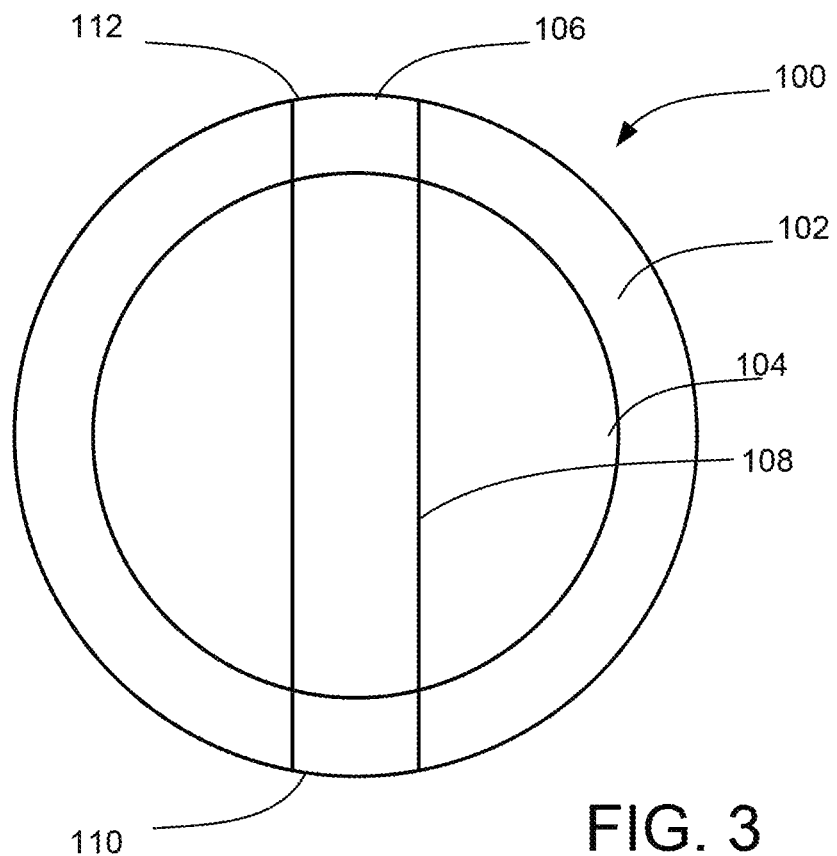
FIG. 3 illustrates a cross-sectional view of a bone taken perpendicularly to the length of bone with a bore extending therethrough according to an embodiment of the present disclosure.
Figure 4:
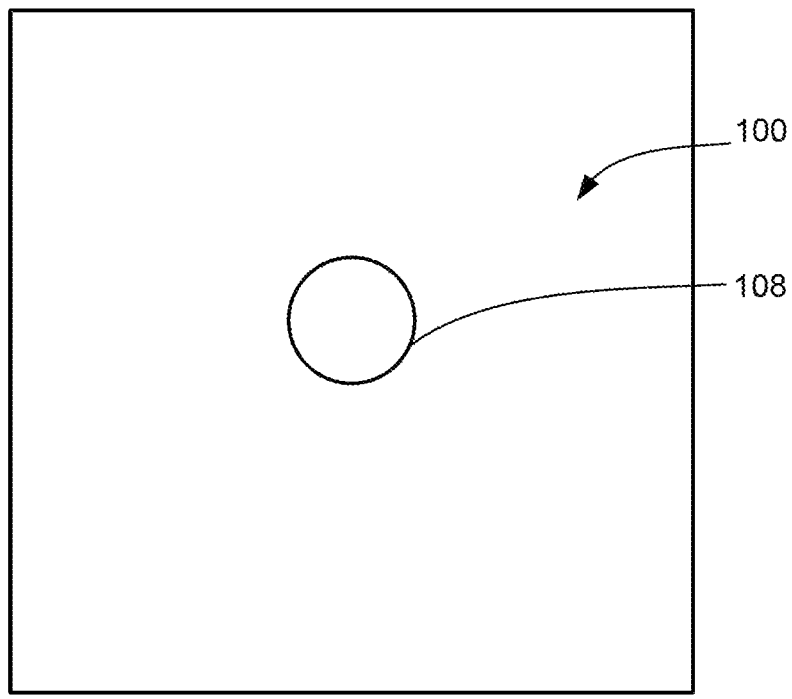
FIG. 4 illustrates an elevation view of the bone of FIG. 3 perpendicular to the cross-sectional view of FIG. 3.
Figure 5:
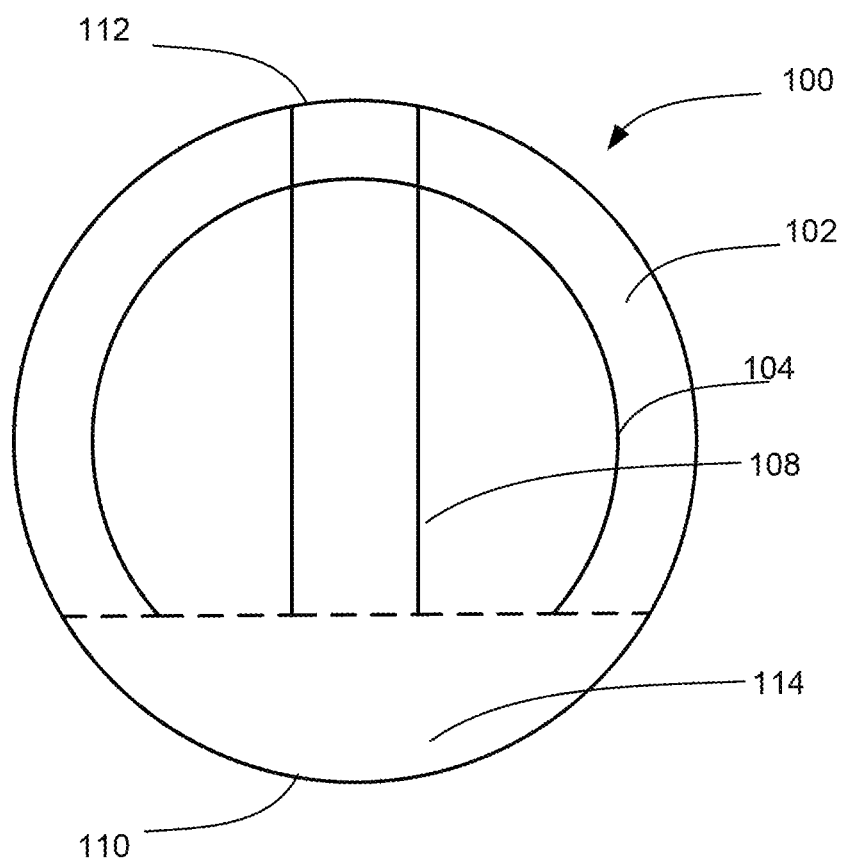
FIG. 5 illustrates a cross-sectional view of a bone taken perpendicularly to the length of the bone in which a lateral cut is made at a first side of the bone according to an embodiment of the present disclosure.

In any regard, the bore 108 may be provided in the bone 100 as is illustrated in the cross-sectional view of FIG. 3 and the elevation view of FIG. 4, in which the drill bit 106 has been retracted from the bore 108. In FIG. 5, an optional lateral cut 114 may be initiated adjacent the first side 110 of the bone 100. As will be appreciated in the following description, the lateral cut 114 may provide a space in which a saw or a portion of a saw may be positioned when the saw is introduced into the bore 108. For instance, the lateral cut 114 may provide spacing for a cutting member when the saw is initially placed in the bore 108. In other embodiments, the lateral cut 114 may not be provided, and the saw may simply be introduced into the bore 108. The lateral cut 114 may be performed using a traditional saw device. As the lateral cut 114 may extend through a portion of the bone 100 extending from the first side 110, the risk that the traditional saw will inadvertently make contact with surrounding soft tissue may be reduced. For instance, given the lateral cut 114 is not to extend entirely through the bone 100, risk of plunge of the traditional saw at the completion of the lateral cut 114 may not be a consideration.

Figure 6:
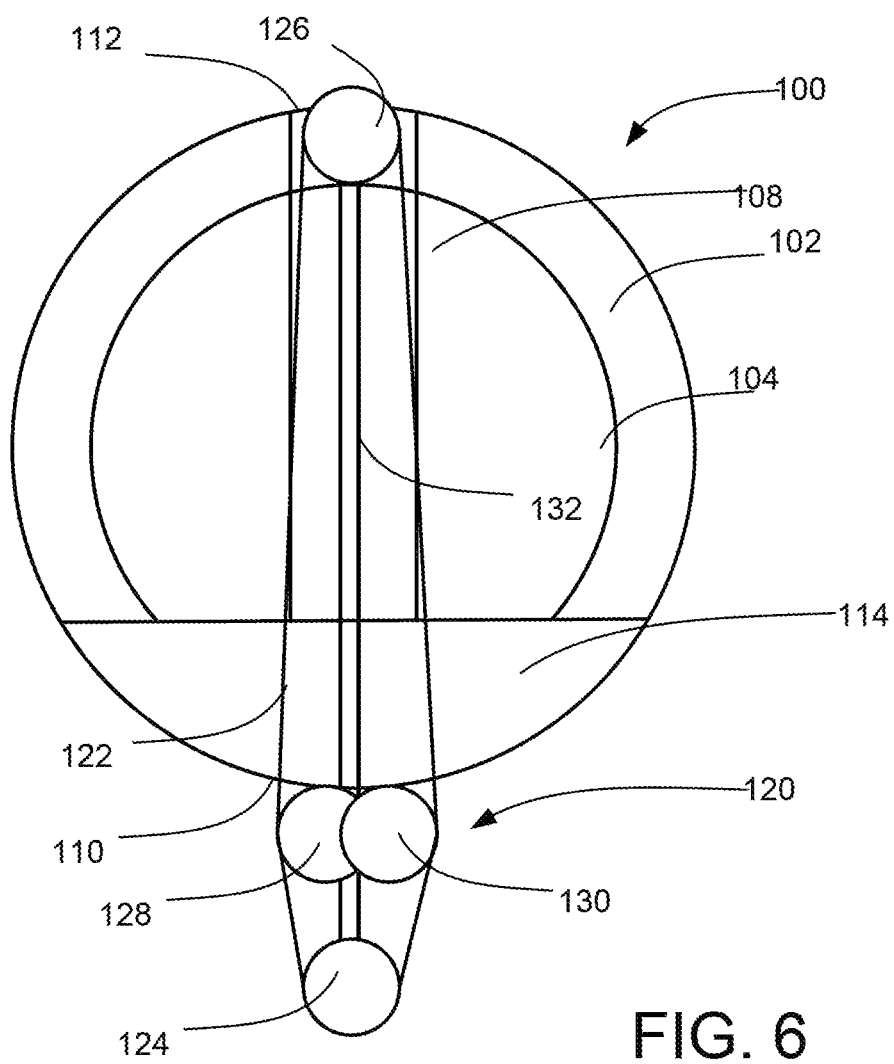
FIG. 6 illustrates a cross-sectional view of a bone taken perpendicularly to the length of the bone in which an embodiment of a saw is inserted into a bore to dispose a cutting member within the bore.
Figure 7:
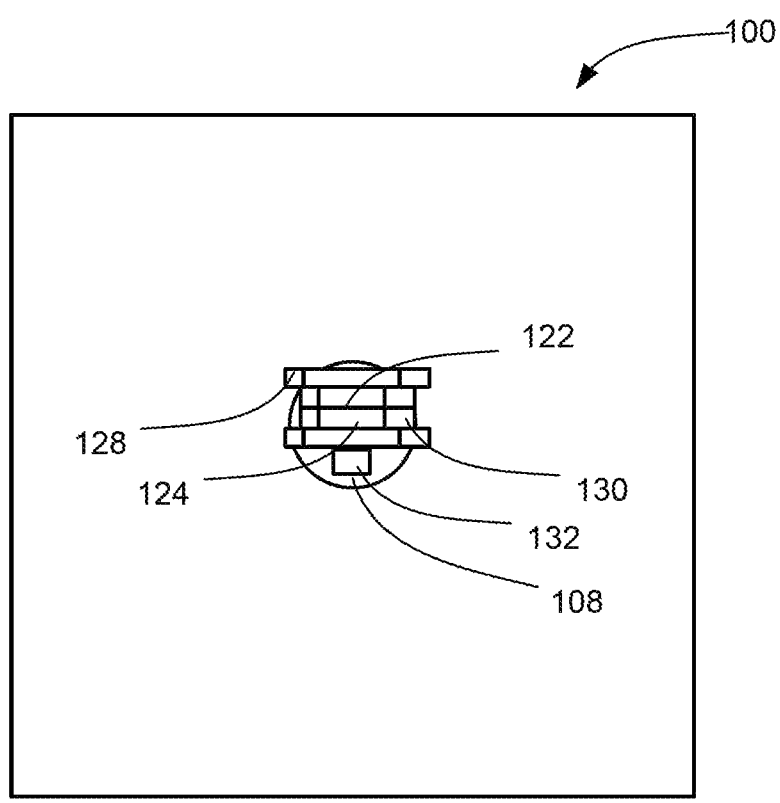
FIG. 7 illustrates an elevation view of the saw as shown in FIG. 6 perpendicular to the cross-sectional view of FIG. 6.
Figure 8:
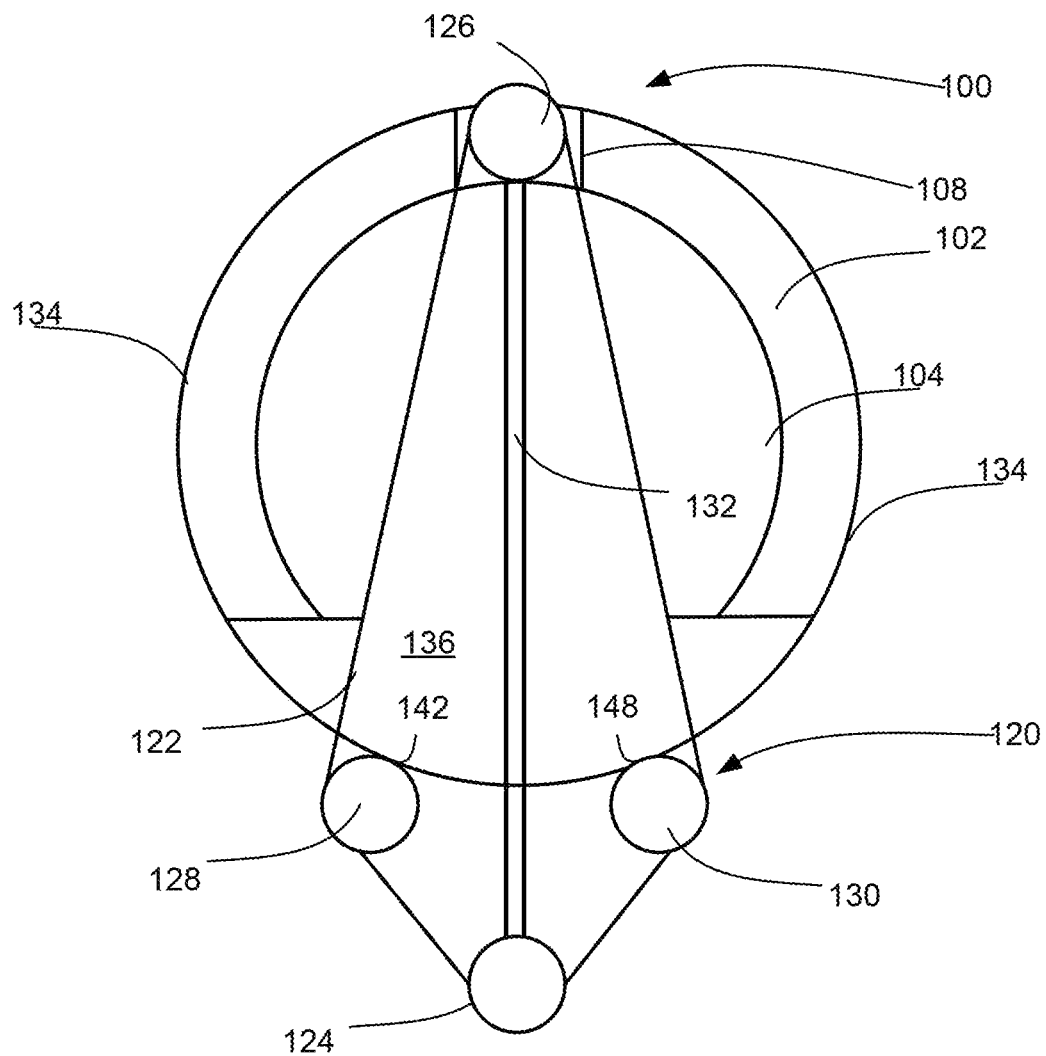
FIG. 8 illustrates the embodiment of the saw of FIG. 6 with guide assemblies in an advanced position to guide the cutting member into contact with the bone.

In FIG. 6, a saw 120 is shown in an inserted position in which a portion of the saw 120 is disposed in the bore 108 in the bone 100. The saw 120 generally includes a cutting member 122. The cutting member 122 may be a flexible material. Specifically, the cutting member 122 may be flexible so that the cutting member 122 may be disposed about a drive pulley 124, an idler pulley 126, a first guide assembly 128, and a second guide assembly 130. The cutting member 122 may also include blades, teeth, abrasive material, or the like, that when moved relative to the bone 100, causes the bone 100 to be cut or otherwise removed adjacent to the cutting member 122. The saw 120 may include a body member 132. The body member 132 may supportably engage the drive pulley 124, idler pulley 126, first guide assembly 128, and second guide assembly 130 as described in greater detail below. For example, support arms (not shown for clarity in FIGS. 6-12, but discussed in greater detail below) may be provided that connect the first guide assembly 128 and the second guide assembly 130, respectively, to the body member 132.

In the arrangement of the saw 120 shown in FIG. 6, the various members of the saw 120 and, at least a portion of the cutting member 122, may be configured for insertion into the bore 108. The saw 120 may be in a first position in which the first guide assembly 128 and the second guide assembly 130 are disposed in a linear or near linear relationship with the idler pulley 126 and the drive pulley 124 to facilitate insertion of the saw 120 into the bore 108. This can be further appreciated in FIG. 7, which depicts an end view of the saw 120 from a proximal position with a view extending distally from an external position relative to the bone 100. Insertion of the saw 120 into the bore 108 may be performed while the cutting member 122 is stationary relative to the drive pulley 124, idler pulley 126, first guide assembly 128, and second guide assembly 130. In this regard, the cutting member 122 may at least partially conform to the bore 108 so as to be disposed therein. Alternatively, the cutting member 122 may be rotated about the drive pulley 124, idler pulley 126, first guide assembly 128, and second guide assembly 130 during insertion, such that any contact to the bore side walls while the saw 120 is advanced into the bore 108 may result in cutting or abrading of the bone 100 where contacted.

In any regard, once disposed in the bore 108, the cutting member 122 may be rotated about the drive pulley 124, idler pulley 126, first guide assembly 128, and second guide assembly 130. For instance, the drive pulley 124 may be engaged with a drive mechanism that may impart rotational movement to the drive pulley 124. In turn, the cutting member 122 may be tensioned such that rotation of the drive pulley 124 results in corresponding rotation of the cutting member 122 relative to the first guide assembly 128, idler pulley 126, and second guide assembly 130. As an example, the drive pulley 124 may engage a tensioner that includes a biasing member to impart a predefined or adjustable tension on the cutting member 122 as it is rotated by the drive pulley 124. The tensioner may allow for selective movement of the drive pulley 124 along the body member 132 to maintain a predetermined or minimum tension on the cutting member 122. In this regard, as the first guide assembly 128 and the second guide assembly 130 move relative to an outer perimeter surface 134 of the bone 100 (in a manner that will be described in greater detail below), the drive pulley 124 may be allowed to move to maintain tension on the cutting member 122. In at least one example, the tensioner may comprise a spring member or other elastomeric body that allows for biased movement of the drive pulley 124 relative to the body member 132.

The first guide assembly 128 and the second guide assembly 130 may be adapted for guiding the cutting member 122 through the bone 100. For instance, the first guide assembly 128 and the second guide assembly 130 may be adapted to bear on an outer perimeter surface 134 of the bone 100. Accordingly, with further reference to FIGS. 8 and 9, the first guide assembly 128 and the second guide assembly 130 are shown in a second position. In the second position, the first guide assembly 128 may be moved in a first direction relative to the outer perimeter surface 134. Also, the second guide assembly 130 may be moved in a second direction relative to the outer perimeter surface 134 in the second position. The movement of the first guide assembly 128 and the second guide assembly 130 may result in the cutting member 122 being forced against the side walls of the bore 108 in response to the movement of the guide assemblies in opposite directions along the outer perimeter surface 134. In turn, the cutting member 122 may begin to cut the bone 100 where the cutting member 122 contactingly engages the bore 108 side wall. In turn, a progressively widening cut 136 may be established between the portion of the cutting member 122 extending between the idler pulley 126 and the first guide assembly 128 and the portion of the cutting member 122 extending between the idler pulley 126 and the second guide assembly 130 as the respective guide members are moved in opposite directions along the outer perimeter surface 134.

Figure 9:
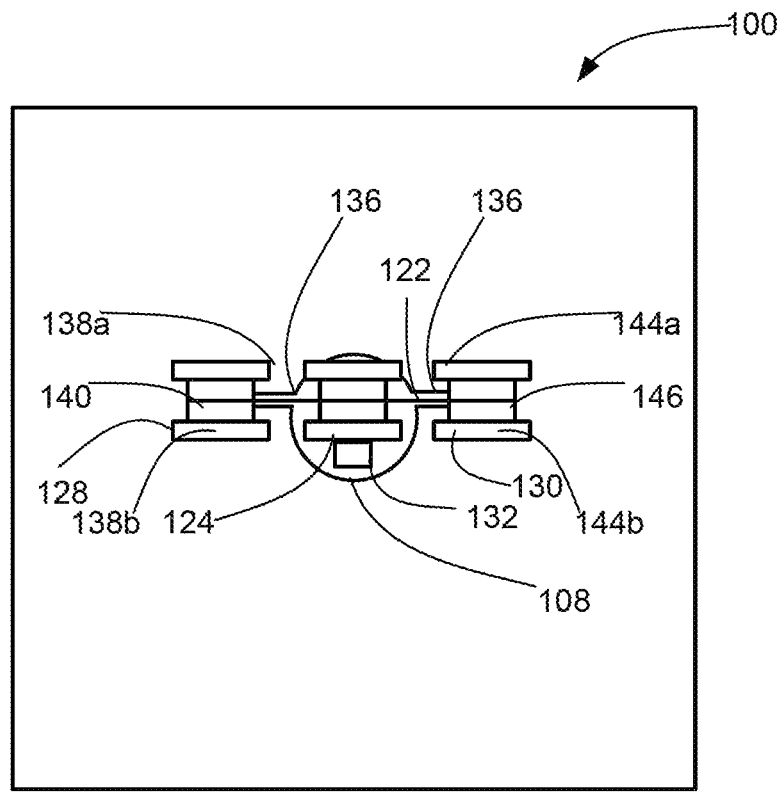
FIG. 9 illustrates an elevation view of the saw as shown in FIG. 8 perpendicular to the cross-sectional view of FIG. 8.

In FIG. 9, a number of details regarding the first guide assembly 128 and the second guide assembly 130 are described. The first guide assembly 128 may include a perimeter bearing portion 138 and a guide pulley 140. The perimeter bearing portion 138 may be adapted to move along the outer perimeter surface 134 of the bone 100. The perimeter bearing portion 138 may have a bearing surface 142 (shown in FIG. 10) that is in contact with the outer perimeter surface 134 of the bone 100. The bearing surface 142 may be adapted to maintain contacting engagement with the outer perimeter surface 134, while also facilitating the movement of the first guide assembly 128 in the first direction about the outer perimeter surface 134. For instance, the bearing surface 142 may have a surface treatment that allows for low friction movement between the bearing surface 142 and the outer perimeter surface 134. In other embodiments, the bearing surface 142 may comprise a roller bearing or the like that allows for movement of the first guide assembly 128 along the outer perimeter surface 134. For instance, as described above, in certain contexts, the bone 100 to be cut may be generally cylindrical such as in the case of common long bones in the body. In such instances, the bone 100 may have a generally cylindrical shape such that the outer perimeter surface corresponds to a cylindrical body.

In any regard, the perimeter bearing portion 138 may be offset from the guide pulley 140. Also, the guide pulley 140 may be independently rotatable relative to the perimeter bearing portion 138 to facilitate movement (e.g., rotation) of the cutting member 122 and the guide pulley 140 relative to the perimeter bearing portion 138. For instance, as best appreciated in FIG. 9, the perimeter bearing portion 138 may be offset from the guide pulley 140 corresponding to the axial direction along the bone 100 (i.e., perpendicular to the direction of the bore 108). Accordingly, the perimeter bearing portion 138 may be disposed offset from the cut 136 such that the perimeter bearing portion 138 maintains engagement with the outer perimeter surface 134 even when the cut 136 is made. The perimeter bearing portion 138 may include a first perimeter bearing portion 138a and a second perimeter bearing portion 138b that may be provided on opposite sides of the cut 136 to assist in support of the guide pulley 140, while allowing free movement of the guide pulley 140 and the cutting member 122 relative to the first perimeter bearing portion 138a and the second perimeter bearing portion 138b.

The second guide assembly 130 may include a perimeter bearing portion 144 and a guide pulley 146. The perimeter bearing portion 144 may be adapted to move along the outer perimeter surface 134 of the bone 100. The perimeter bearing portion 144 may have a bearing surface 148 (shown in FIG. 10) that is in contact with the outer perimeter surface 134 of the bone 100. The bearing surface 148 may be adapted to maintain contacting engagement with the outer perimeter surface 134, while also facilitating the movement of the second guide assembly 130 in the second direction about the outer perimeter surface 134. For instance, the bearing surface 148 may have a surface treatment that allows for low friction movement between the bearing surface 148 and the outer perimeter surface 134. In other embodiments, the bearing surface 148 may comprise a roller bearing or the like that allows for movement of the second guide assembly 130 along the outer perimeter surface 134.

The perimeter bearing portion 144 may be offset from the guide pulley 146. Also, the guide pulley 146 may be independently rotatable relative to the perimeter bearing portion 144 to facilitate movement (e.g., rotation) of the cutting member 122 and the guide pulley 146 relative to the perimeter bearing portion 144. For instance, as best appreciated in FIG. 9, the perimeter bearing portion 144 may be offset from the guide pulley 146 corresponding to the axial direction along the bone 100 (i.e., perpendicular to the direction of the bore 108). Accordingly, the perimeter bearing portion 144 may be disposed offset from the cut 136 such that the perimeter bearing portion 144 maintains engagement with the outer perimeter surface 134 even when the cut 136 is made. The perimeter bearing portion 144 may include a first portion 144a and a second portion 144b that may be provided on opposite sides of the cut 136 to assist in support of the guide pulley 146, while allowing free movement of the guide pulley 140 and the cutting member 122 relative to the first perimeter bearing portion 138a and the second perimeter bearing portion 138b.

Figure 10:
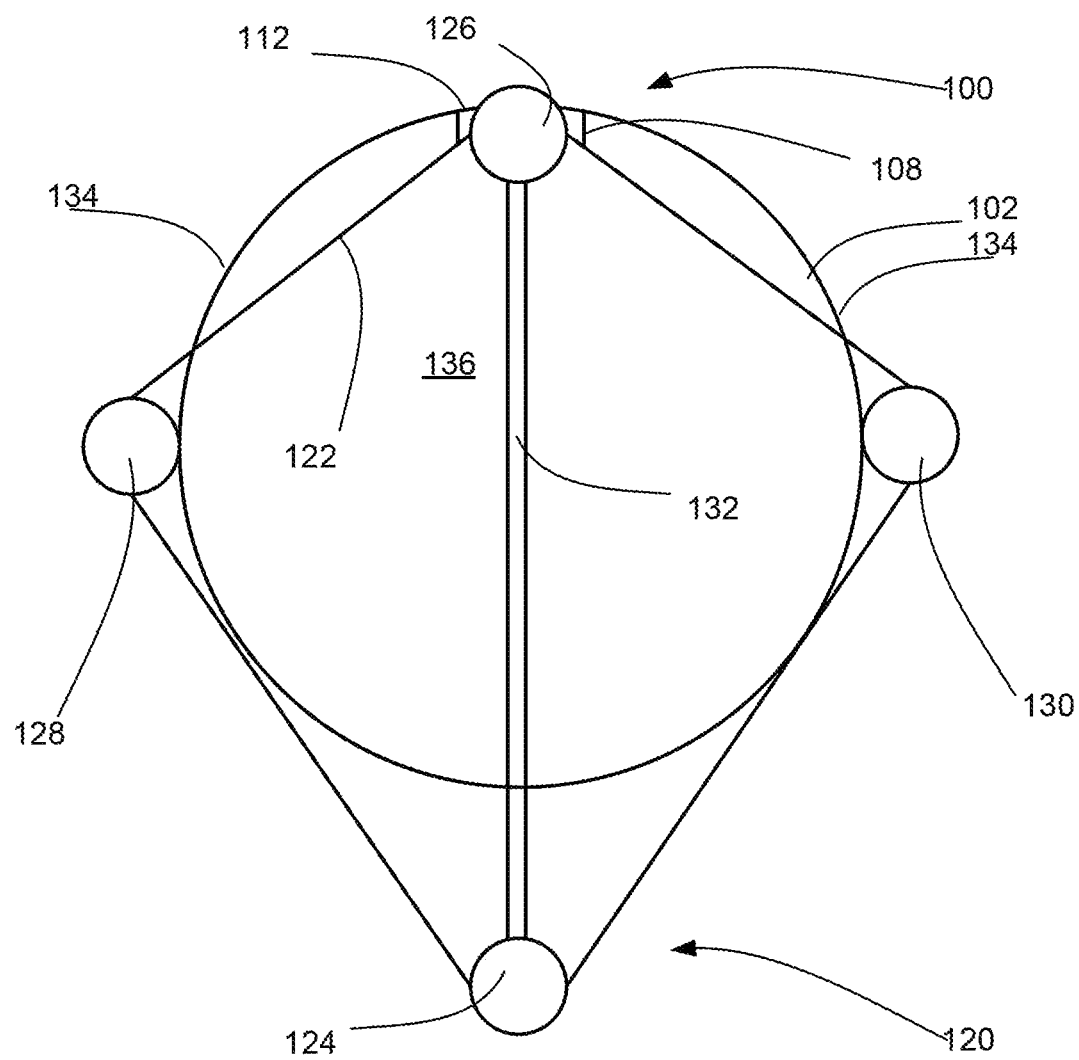
FIG. 10 illustrates the embodiment of the saw of FIG. 6, with guide assemblies in another advanced position.
Figure 11:
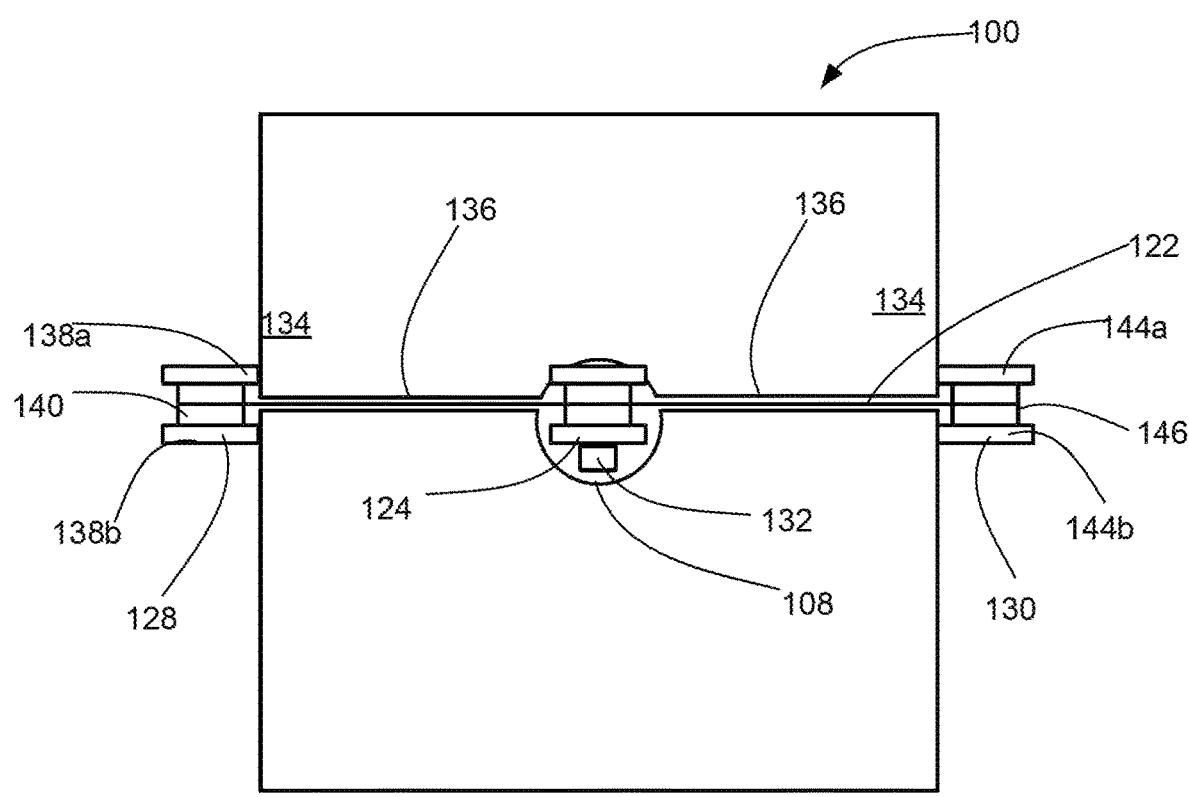
FIG. 11 illustrates an elevation view of the saw as shown in FIG. 10 perpendicular to the cross-sectional view of FIG. 10.
Figure 12:
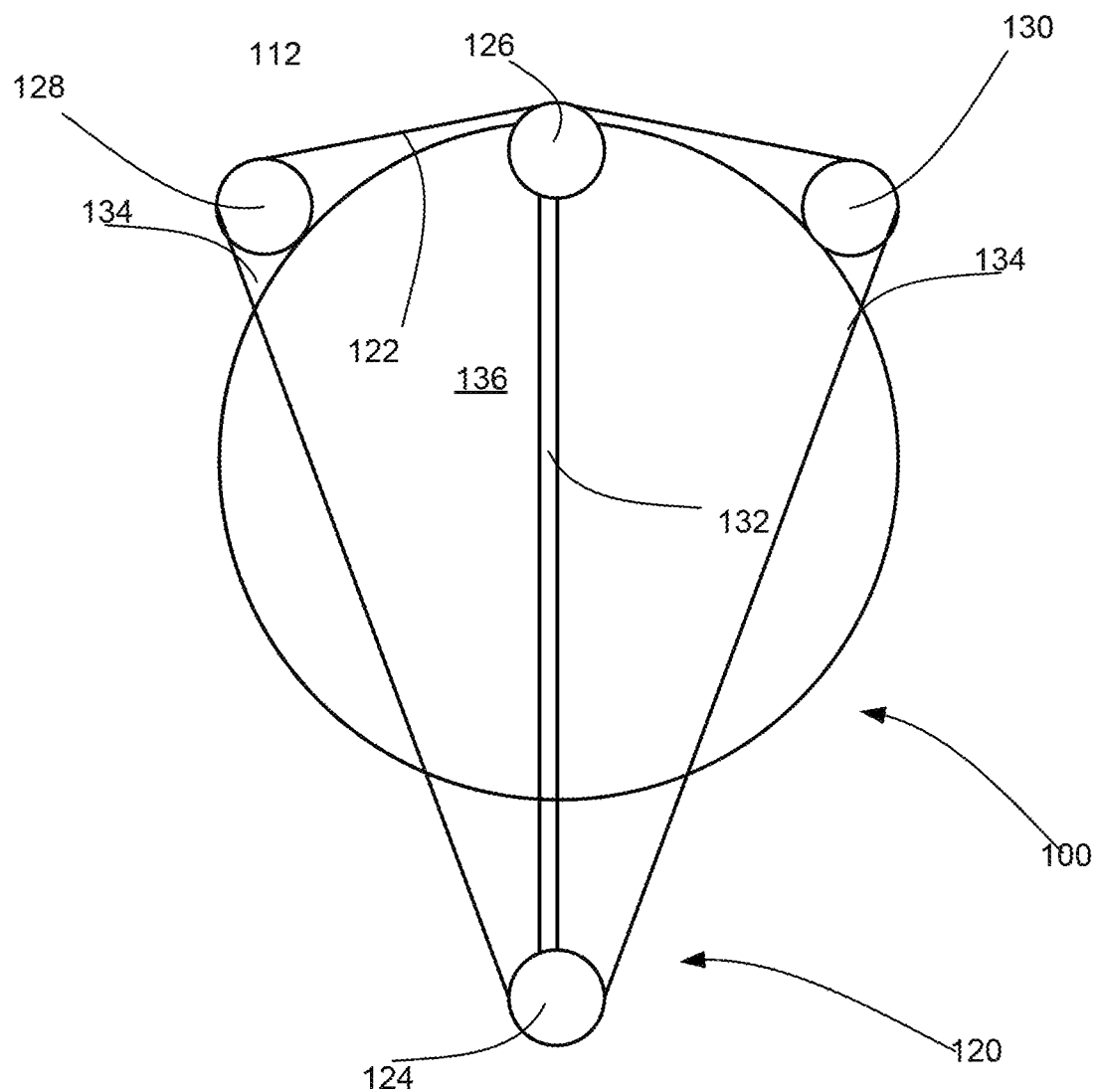
FIG. 12 illustrates the embodiment of the saw of FIG. 6, with guide assemblies in a completed position in which the cutting member has completed a cut through the bone.

As the first guide assembly 128 and the second guide assembly 130 move in opposite directions along the outer perimeter surface 134 of the bone, the cutting member 122 may be progressively contacted with the bone 100 along a sidewall of the bore 108. As such, FIGS. 10 and 11 show the first guide assembly 128 and the second guide assembly 130 in a third position in which the respective guide members has moved further along the outer perimeter surface 134 of the bone 100 in the respective directions of movement. As such, the cut 136 is shown as continuing through the bone. Such progress may be continued until the cutting member 122 passes through the entirety of the bone 100 as shown in FIG. 12, in which the first guide assembly 128 and the second guide assembly 130 are in a fourth position, and the cut 136 extends through the bone 100.

Figure 13:
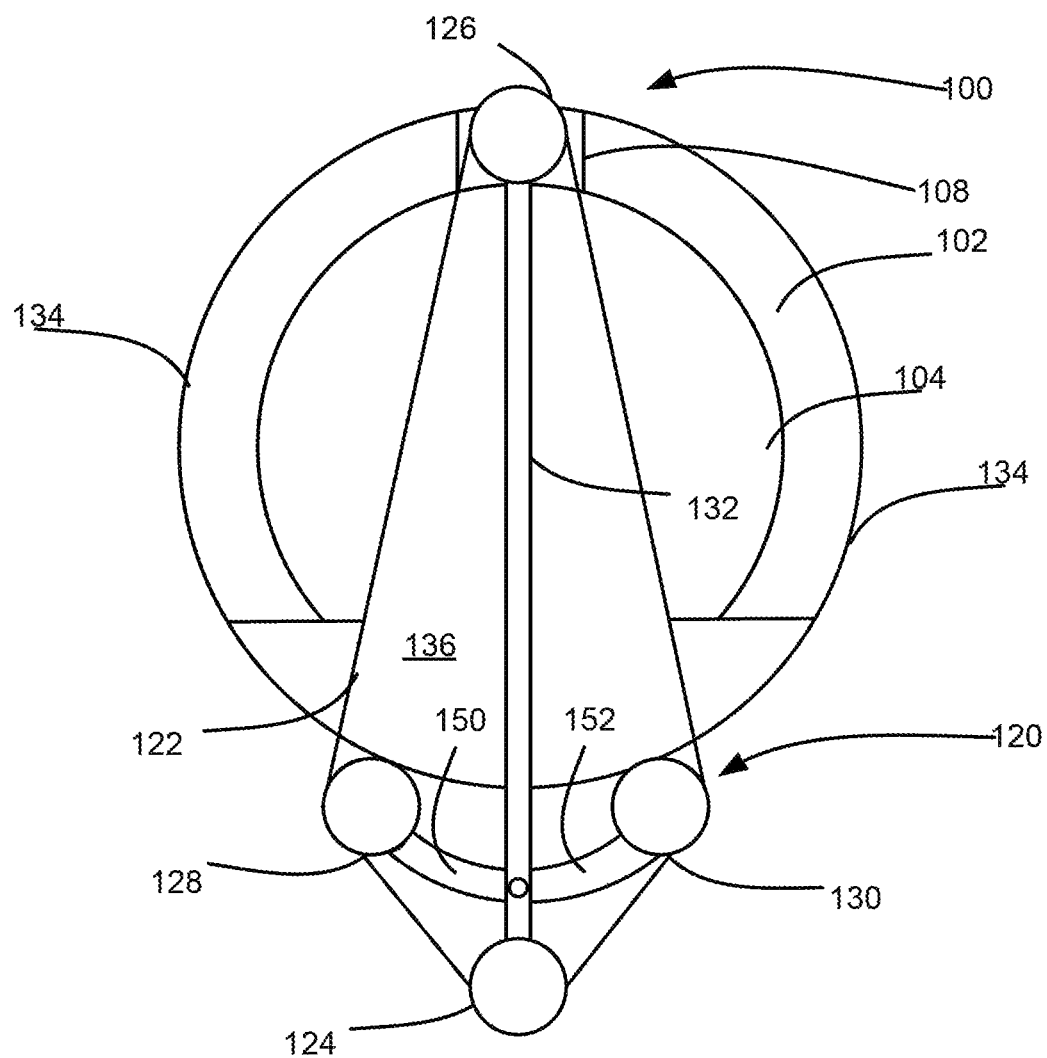
FIG. 13 illustrates an embodiment of a saw having support arms in a first configuration for supporting and biasing guide members into contact with an outer perimeter surface of the bone.
Figure 14:
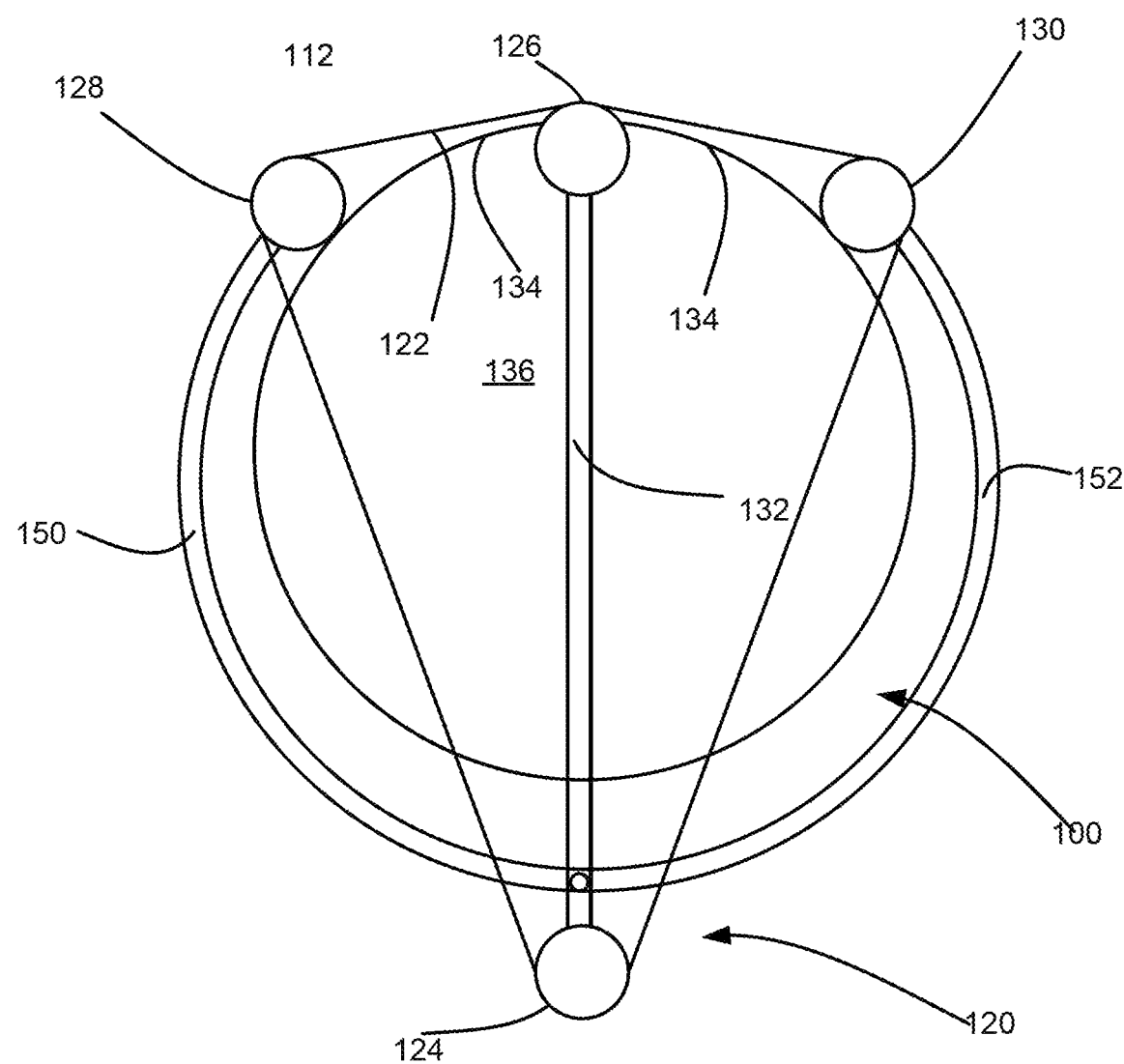
FIG. 14 illustrates the embodiment of the saw of FIG. 13 with the support arms in a second configuration.

While not depicted in the preceding figures, the first guide assembly 128 may be supported by a first support arm 150 and the second guide assembly 130 may be supported by a second support arm 152. One embodiment of such an arrangement is shown in FIGS. 13 and 14. The first guide assembly 128 may be disposed at a distal portion of the first support arm 150. A proximal portion of the first support arm 150 may be engaged with the body member 132. For instance, the first support arm 150 may be pivotally engaged with the body member 132 such that the first support arm 150 is pivotal relative to the body member 132. The engagement of the first support arm 150 may further facilitate the movement of the first guide assembly 128 about the outer perimeter surface 134.

Similarly, the second guide assembly 130 may be disposed at a distal portion of the second support arm 152. A proximal portion of the second support arm 152 may be engaged with the body member 132. For instance, the second support arm 152 may be pivotally engaged with the body member 132 such that the second support arm 152 is pivotal relative to the body member 132. The engagement of the second support arm 152 may further facilitate the movement of the second guide assembly 130 about the outer perimeter surface 134.

In FIG. 13, where the guide members are shown in a second position that is intermediate in the cutting of the bone 100, the first support arm 150 and the second support arm 152 may be in a compressed or partially collapsed state. In FIG. 14, where the guide members are in a fourth position where the cut of the bone 100 is complete, the first support arm 150 and the second support arm 152 may be in an extended or expanded position. In turn, the support arms may be telescopic or otherwise extendable or expandable to facilitate the movement of the guide members about the outer perimeter surface 134 of the bone 100. Additionally, the first support arm 150 and the second support arm 152 may be shaped to avoid interference with the bone 100, while allowing the respective ones of the guide assemblies to move unobstructed about the outer perimeter surface 134. Alternatively, the first support arm 150 and the second support arm 152 may be flexible or otherwise adaptable to support the guide assemblies as the guide assemblies move about the outer perimeter surface 134 of the bone while maintaining contact between the guide assemblies and the outer perimeter surface 134. As shown in FIG. 13, the first support arm 150 and the second support arm 152 may be connected to the body member 132. The first support arm 150 and the second support arm 152 may be moveable relative to the body member 132 at a common axis or may be located separately on the body member 132.

Also, one or more biasing members (not shown) may engage, directly or indirectly, the guide members to maintain the guide members in contacting engagement with the outer perimeter surface 134 of the bone. In one example, one or more biasing members may be engaged with the first support arm 150 or the second support arm 152 to maintain the first guide assembly 128 and the second guide assembly 130 in contacting engagement with the bone 100. The biasing members may comprise a spring, elastomeric member, or another appropriate device that may produce a biasing force to act on the guide members to dispose the guide members in contacting engagement with the outer perimeter surface 134 of the bone 100. The one or more biasing members may act individually on respective ones of the support arms or may span between the support arms (e.g., to apply a biasing force that urges the support arms toward one another).

Figure 15:
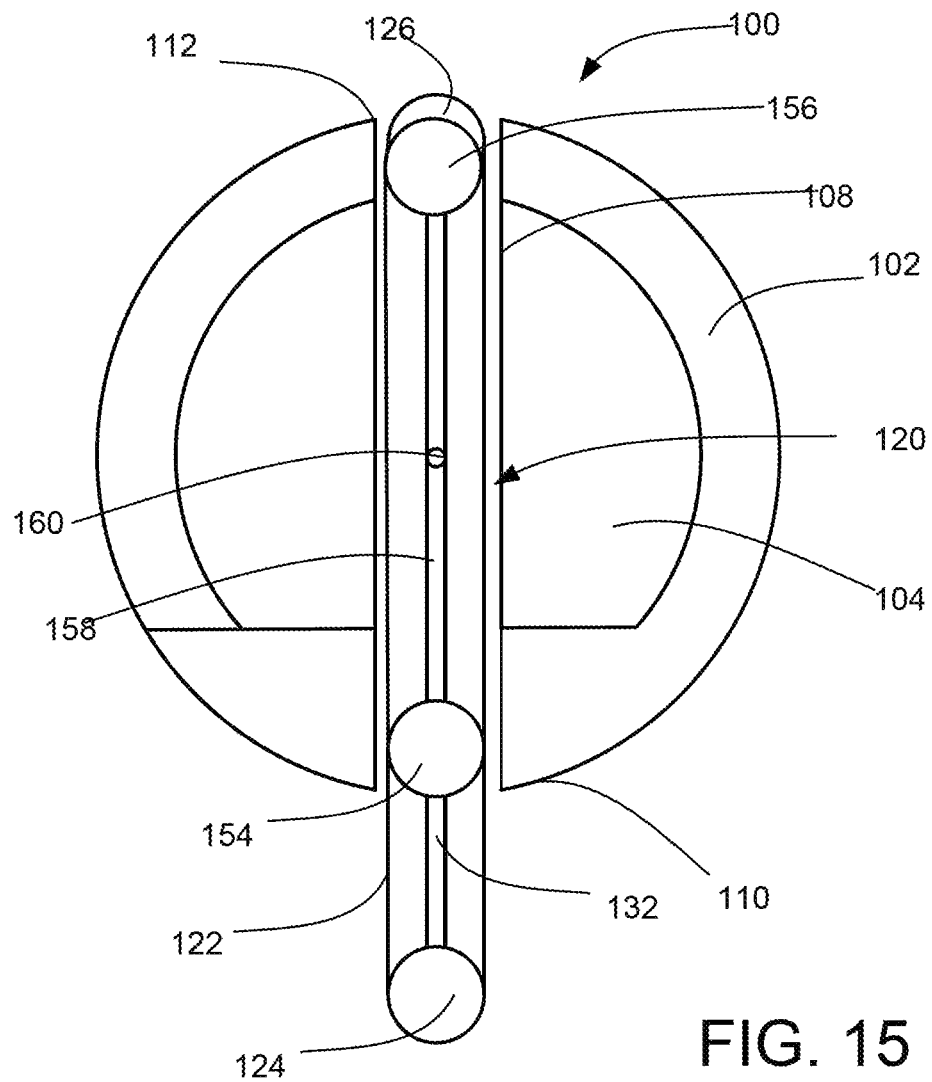
FIG. 15 illustrates a cross-sectional view of a bone taken perpendicularly to the length of the bone in which another embodiment of a saw is inserted into a bore in a first position to dispose a cutting member in the bore.
Figure 16:
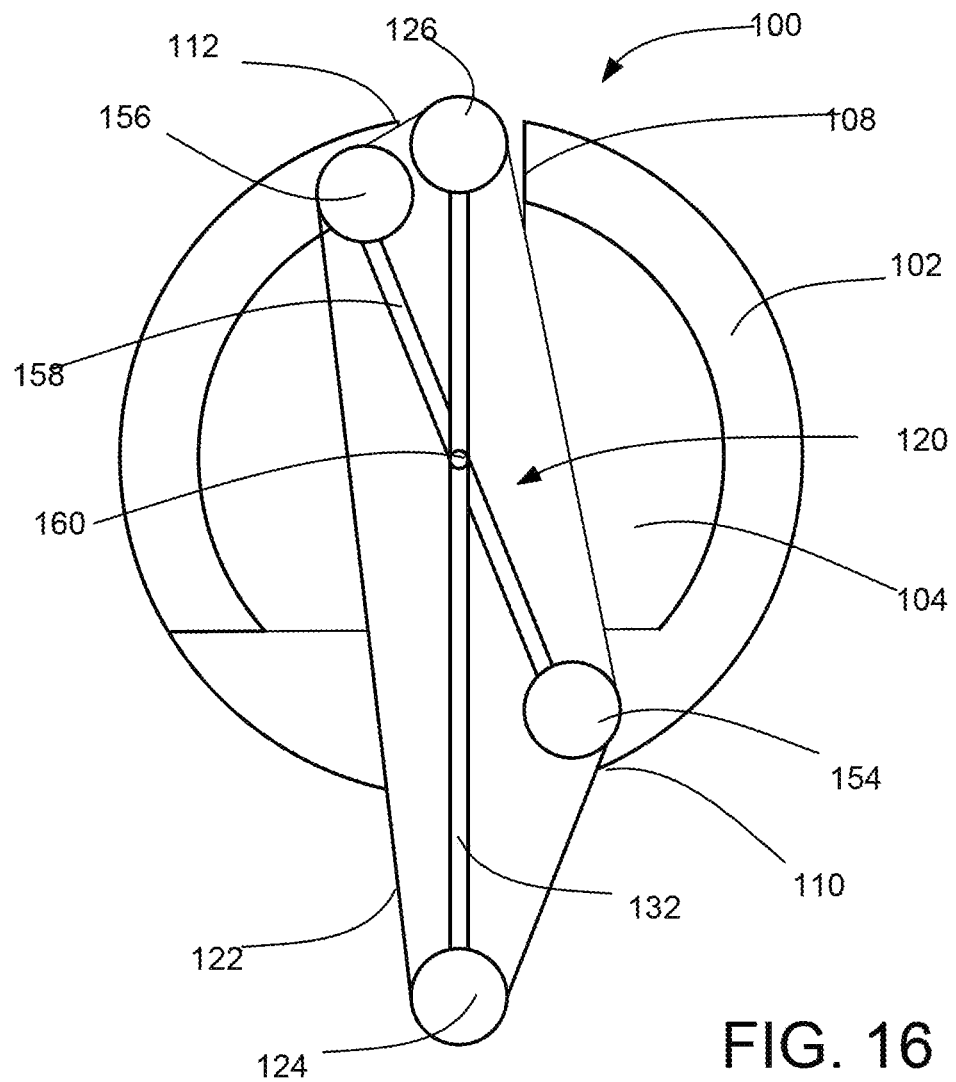
FIG. 16 illustrates the embodiment of FIG. 15 in a second position in which the guide pulleys of the saw have been moved through a first range of movement.
Figure 17:
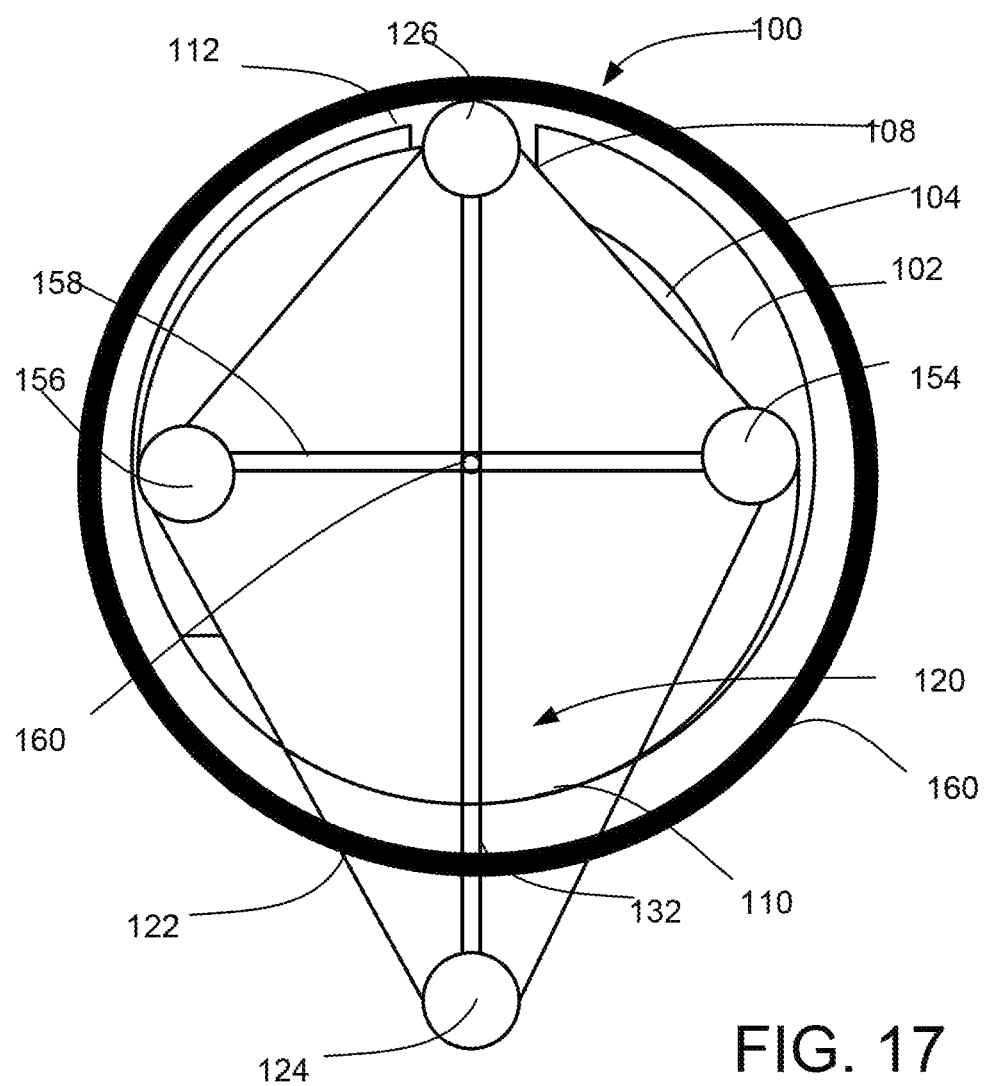
FIG. 17 illustrates the embodiment of FIG. 15 in a third position in which the guide pulleys of the saw have been moved through a second range of movement.

In another embodiment, guide members may be provided that are moved within a cross-sectional envelope of the bone rather than along an outer perimeter surface of a bone. With further reference to FIGS. 15-17, such an embodiment of a saw 120 is shown. In FIG. 15, the saw 120 may be inserted into a bore 108 created in the bone 100. The saw 120 may be in a first position such that an idler pulley 126, drive pulley 124, first guide assembly 154 and second guide assembly 156 are substantially colinear. The configuration of the saw 120 shown in FIG. 15 may facilitate insertion of the saw 120 into the bore. As the cutting member 122 may be disposed about the idler pulley 126, drive pulley 124, first guide assembly 154, and second guide assembly 156, the cutting member 122 may at least partially be disposed in the bore 108.

The first guide assembly 154 may comprise a first guide pulley about which the cutting member 122 is disposed. The second guide assembly 156 may comprise a second guide pulley about which the cutting member 122 is disposed. In this regard, like the embodiments described above, the cutting member 122 may be rotatable about the pulleys (e.g., be driven by the drive pulley 124). The cutting member 122 may also be tensioned in any manner described above.

The first guide assembly 154 may be supportably engaged by a rotating support member 158. The second guide assembly 156 may be supportably engaged by the rotating support member 158 as well. However, in other embodiments, the first guide assembly 154 and the second guide assembly 156 may be supportably engaged with independent support arms. In the embodiment shown in FIGS. 15-17, the first guide assembly 154 and the second guide assembly 156 are disposed on opposite sides of a rotating support member 158, which is rotatably engaged with the body member 132 at an interconnection 172.

The rotating support member 158 may be moved relative to the body member 132 as shown in FIG. 16, the rotating member 158 has been moved counterclockwise to a second position. In doing so, the first guide assembly 154 and the second guide assembly 156 are correspondingly moved. The cutting member 122 is forced against the sidewall of the bore 108 to cut the bone 100. In addition to the cutting member 122, the first guide assembly 154 and the second guide assembly 156 may include cutting features. For instance, the periphery of the first guide assembly 154 and/or the second guide assembly 156 may have cutting teeth or the like. In this regard, the first guide assembly 154 and second guide assembly 156 may act upon the bone 100 to cut the same. The first guide assembly 154 and the second guide assembly 156 may also urge the cutting member 122 that extends between adjacent pulleys of the saw 120 against the bone 100 to cut the bone 100.

Accordingly, with further reference to FIG. 17, the rotating member 158 is disposed in a third position in which the first guide assembly 154 and the second guide assembly 156 have been advanced relative to the second position of FIG. 16. As can be appreciated, the cutting of the bone 100 may continue until the first guide assembly 154 and second guide assembly 156 are rotated completely or partially about the interconnection 172.

The approach depicted in FIGS. 15-17 may result in minimal eruption of the guide assemblies and/or cutting member 122 from the outer perimeter surface of the bone 100. As a result, a small amount of the outer cortex layer 102 may be left upon completion of the cut. Such remaining layer may be easily separated with minimal trauma to surrounding soft tissue. Moreover, the length of the rotating member 158 (e.g., on either or both sides of the rotating member 158 engaged with the first guide assembly 154 and the second guide assembly 156, respectively) may be controlled to maintain the guide assemblies at or near the outer perimeter surface to achieve as complete a cut as possible. For instance, the rotating member 158 may be telescoping or otherwise configured to adjust the total length thereof or the length of either portion on respective opposite sides of the interconnection 172.

While controlling the length of the rotating member 158 or the length/movement of any other supporting member that supportably engages the first guide assembly 154 and the second guide assembly 156, it may be beneficial to provide further protection to surrounding soft tissue. In this regard, a collar 160 may be positioned about the exterior of the bone 100. The collar 160 may be disposed close to the exterior of the bone 100 to minimize the amount of soft tissue movement or trauma experienced due to positioning the collar 160. The collar 160 may be made from a material that is harder than the bone 100, and which resists being cut by the cutting member 122 and/or the cutting features of a guide assembly. In this regard, the guide assemblies may be biased toward contacting engagement with the collar 160. In this regard, as the rotating member 158 is rotated, the cutting member 122 and/or the cutting features of the guide assemblies may cut through the bone 100 until the respective cutting mechanism contacts the inner surface of the collar 160. Contact with the inner surface of the collar 160 may prevent or reduce the likelihood that the cutting mechanism contacts surrounding soft tissue to cause damage to it. That is, as the cutting member 122 and/or cutting features of the guide assemblies may not cut through the collar 160, the bone 100 may be cut such that the cutting mechanism erupts through the outer perimeter surface of the bone 100 and contacts the collar 160 rather than further extending into any surrounding soft tissue.

Figure 18:
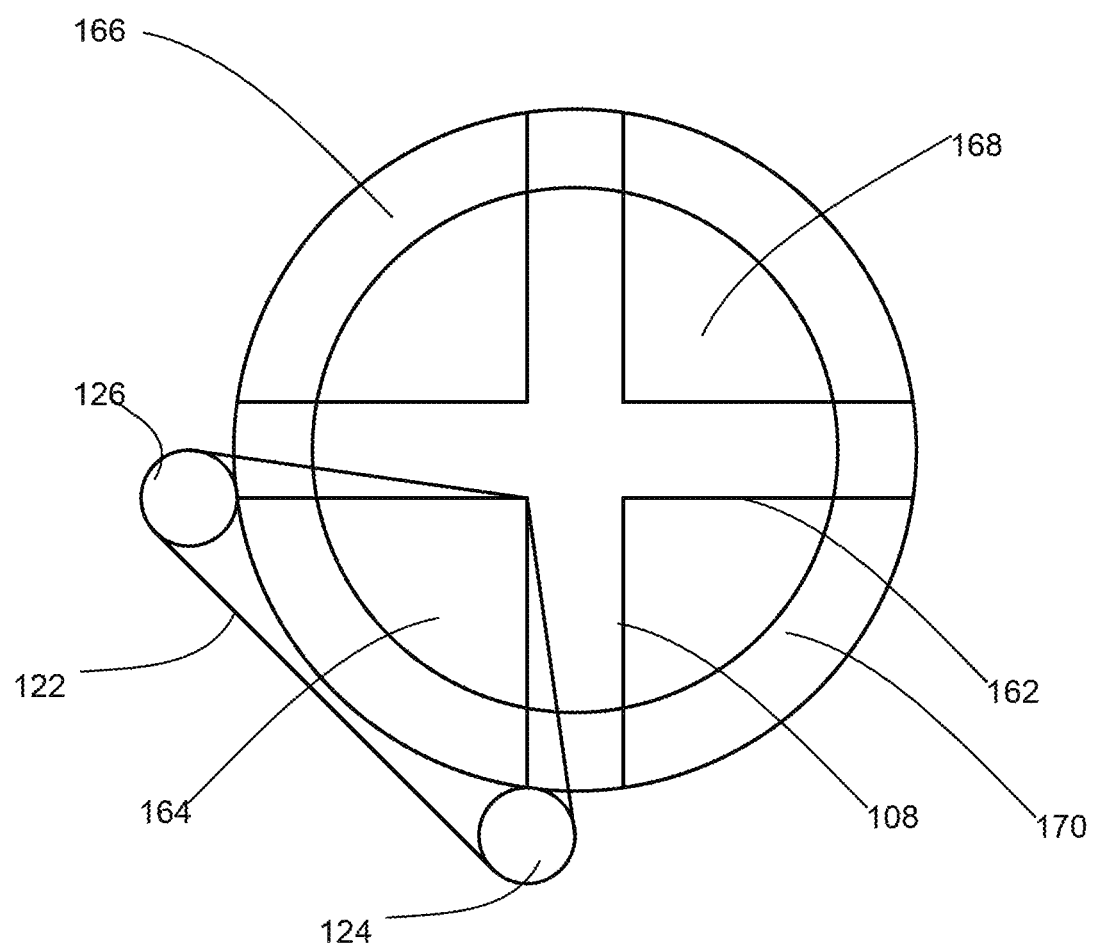
FIG. 18 illustrates a cross-sectional view of a bone in which perpendicular bores are formed for routing of a cutting member with respect to the bone.

In the preceding embodiments, the saw is introduced into a bore 108 extending through the bone. In other embodiments, a plurality of bores may be created in a bone 100 to facilitate the introduction of a cutting member 122 to the one or more bores for cutting the bone. For instance, as shown in FIG. 18, a second bore 162 may be created perpendicular to a bore 108. In turn, the bone 100 may be divided into a first quadrant 164, a second quadrant 166, a third quadrant 168, and a fourth quadrant 170. In this regard, a drive pulley 124 may be disposed near the end portion of the bore 108. At least one idler pulley 126 may be disposed near the end portion of the second bore 162. In turn, a cutting member 122 may be provided such that it extends through a first portion of the bore 108 and a second portion of the second bore 162. Also, the cutting member 122 may extend about the idler pulley 126 and the drive pulley 124. In turn, the cutting member 122 may be rotated and increased tension applied to the cutting member 122 (e.g., by the movement of the drive pulley 124 and/or idler pulley 126) may cause the cutting member 122 to contact and cut through the first quadrant 164. The idler pulley 126 and the drive pulley 124 may be repositioned to others of the quadrants to complete cuts relative to the remaining quadrants.

Figure 19:
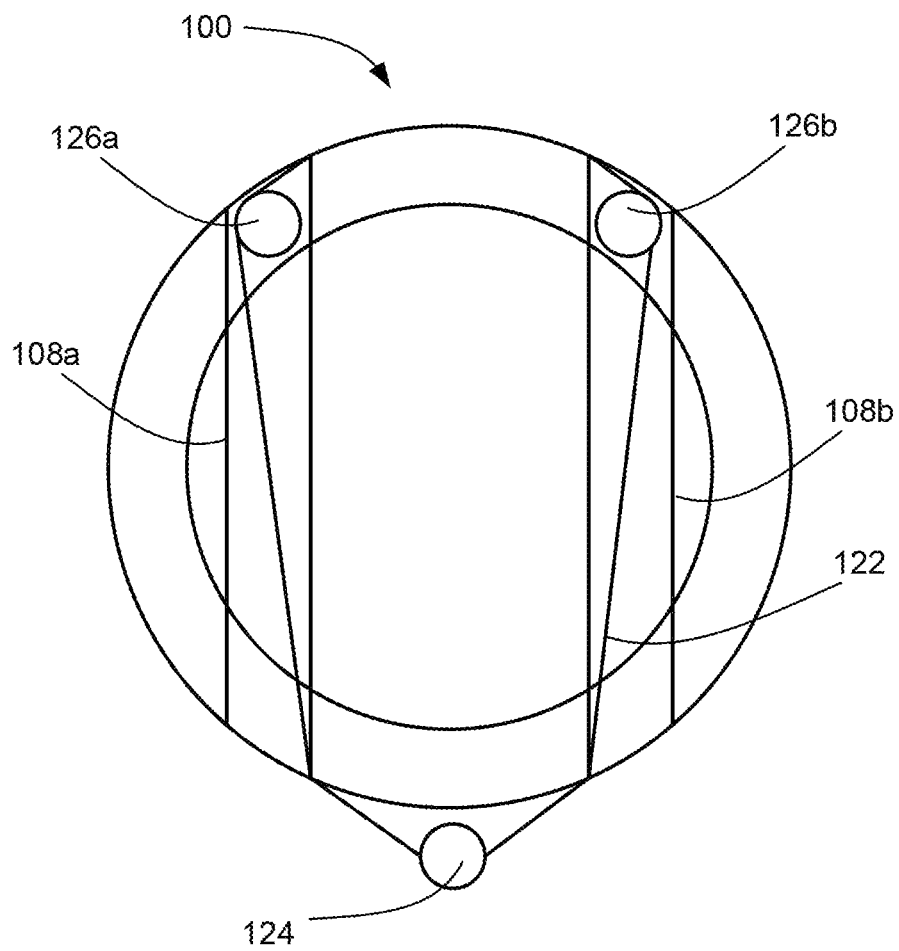
FIG. 19 illustrates a cross-sectional view of a bone in which a plurality of chord bores are formed for routing of a cutting member with respect to the bone.

FIG. 19 illustrates another embodiment for cutting a bone 100. A first bore 108a and a second bore 108b may be created in the bone 100. While the first bore 108a and the second bore 108b are shown as being parallel, this need not be the case as the first bore 108a and the second bore 108b may be created in any relative orientation. In any regard, a drive pulley 124 may engage a cutting member 122. The cutting member 122 may extend between the drive pulley 124 and a first idler pulley 126a. The cutting member 122 may be disposed in the first bore 108a along the length of the cutting member 122 between the drive pulley 124 and the first idler pulley 126a. The cutting member 122 may extend between the first idler pulley 126a and a second idler pulley 126b. The cutting member may also extend between the second idler pulley 126b and the drive pulley 124 such that the portion of the cutting member 122 between the second idler pulley 126b and the drive pulley 124 extends through the second bore 108b. As such, upon tensioning of the cutting member 122, the cutting member 122 may engage a portion of the bone 100 between the first bore 108a and the second bore 108b. In turn, the portion between the first bore 108a and the second bore 108b may be cut. In turn, the outer portions of the bone 100 extending from the first bore 108a to a first edge of the bone 100 and from the second bore 108b to a second edge of the bone 100 may also be cut (e.g., using an approach as described in FIG. 18 using a drive pulley 124 and an idler pulley 126). As such, all or a portion of the bone 100 may be severed.

The preceding description has been presented for purposes of illustration and description. Furthermore, the description is not intended to limit the claims to the form disclosed herein. Consequently, variations and modifications commensurate with the above teachings, and skill and knowledge of the relevant art are within the scope of the present disclosure. The embodiments described hereinabove are further intended to explain known modes of practicing the disclosure and to enable others skilled in the art to utilize the disclosure in such or other embodiments and with various modifications required by the particular application (s) or use(s) of the present disclosure. It is intended that the appended claims be construed to include alternative embodiments to the extent permitted by the prior art.

What is claimed is:

1. A saw for cutting through a bone, comprising:
a drive pulley that is positionable at a first location relative to the bone;
an idler pulley that is positionable at a second location relative to the bone; and
a cutting member that is positionable to extends through a bore that extends at least partially through the bone, that the cutting member is rotatable relative to the drive pulley and the idler pulley to contact a sidewall of the bore through which the cutting member extends to cut the bone, wherein the cutting member extends at least partially through a first bore and at least partially through a second bore, and wherein the first bore and the second bore intersect.

2. The saw of claim 1, further comprising:
a tensioner engaged with the cutting member to maintain tension on the cutting member.

3. The saw of claim 2, wherein the tensioner is engaged with the drive pulley to impart the tension on the cutting member.

4. The saw of claim 1, wherein the first bore and the second bore do not intersect.

5. A saw for cutting through a bone, comprising:
a drive pulley operatively engaged with a cutting member and positionable at a first side of the bone to be cut;
an idler pulley positionable at a second side of the bone that is opposite the first side, wherein the idler pulley is passed through a bore extending through the bone to be positioned at the second side, and wherein the cutting member is engaged with the idler pulley such that the cutting member extends through the bore between the drive pulley and the idler pulley;
a first guide assembly comprising:
a first guide pulley engaged with the cutting member between the idler pulley and the drive pulley, and
a first perimeter bearing contactingly engageable with an outer perimeter surface of the bone and adapted to maintain contacting engagement with the outer perimeter surface while moving in a first direction along the outer perimeter surface;
a second guide assembly comprising:
a second guide pulley engaged with the cutting member between the idler pulley and the drive pulley, and
a second perimeter bearing contactingly engageable with the outer perimeter surface and adapted to maintain contacting engagement with the outer perimeter surface while moving in a second direction opposite the first direction; and
a drive mechanism engaged with the drive pulley to cause movement of the cutting member around the drive pulley, first guide pulley, idler pulley, and second guide pulley, wherein the first guide assembly and the second guide assembly are moveable about the outer perimeter surface to contact the bone with the cutting member as the first guide assembly and the second guide assembly moves along the outer perimeter surface of the bone.

6. The saw of claim 5, further comprising:
a tensioner engaged with the cutting member to maintain tension on the cutting member as the first guide assembly and the second guide assembly moves along the outer perimeter of the bone.

7. The saw of claim 6, wherein the tensioner is engaged with the drive pulley to impart the tension on the cutting member.

8. The saw of claim 7, wherein the bone comprises a cylindrical outer perimeter surface, and the first direction comprises a first circumferential direction and the second direction comprises a second circumferential direction.

9. The saw of claim 8, further comprising:
a first biasing member acting on the first guide assembly to maintain the first perimeter bearing in contacting engagement with the outer perimeter surface as the first guide assembly moves along the outer perimeter surface in the first direction; and
a second biasing member acting on the second guide assembly to maintain the second perimeter bearing in contacting engagement with the outer perimeter surface as the second guide assembly moves along the outer surface perimeter in the second direction.

10. The saw of claim 9, wherein the first guide assembly moves along the cylindrical outer perimeter from adjacent the drive pulley to adjacent the idler pulley in the first circumferential direction and the second guide assembly moves along the cylindrical outer perimeter from adjacent the drive pulley to adjacent the idler pulley in the second circumferential direction.

11. The saw of claim 10, wherein the first perimeter bearing comprises at least one bearing surface and the second perimeter bearing comprises at least another bearing surface.

12. The saw of claim 11, wherein the at least one bearing surface of each of the first perimeter bearing and the second perimeter bearing is offset in a direction corresponding to an axial direction of the cylindrical outer perimeter from the respective one of the first guide pulley or the second guide pulley such that the respective bearing surface maintains contacting engagement with the cylindrical outer perimeter adjacent to a portion of the bone cut by the cutting member.

13. The saw of claim 9, wherein the first guide assembly is disposed at a distal end of a first support arm that is pivotally displaceable from a proximal end of the first support arm and the second guide assembly is disposed at a distal end of a second support arm that is pivotally displaceable from a proximal end of the second support arm.

14. The saw of claim 13, wherein the first biasing member acts on the first support arm and the second biasing member acts on the second support arm to bias the first and second guide assemblies toward one other.

15. The saw of claim 14, wherein action of respective ones of the first biasing member on the first support arm and the second biasing member on the second support arm results in at least a component force vector on the first and second guide assemblies in a radial direction relative to the cylindrical outer perimeter.

16. The saw of claim 15, wherein the idler pulley and the drive pulley are mounted on a body member, which is located in the bore to dispose the drive pulley at the first side of the bone and the idler pulley at the second side of the bone.

17. The saw of claim 16, wherein the proximal end of the first support arm and the proximal end of the second support arm are pivotally engaged with the body member.

18. The saw of claim 17, wherein the proximal end of the first support arm and the proximal end of the second support arm are pivotal about a common axis of the drive pulley.

19. The saw of claim 18, wherein the tensioner allows the drive pulley, the first support arm, and the second support arm to move relative to the idler pulley to maintain tension on the cutting member.

20. The saw of claim 19, wherein the tensioner comprises a spring member between the drive pulley and the idler pulley.

21. The saw of claim 5, wherein the bore comprises a drill hole created by drilling through the bone from the first side of the bone to the second side of the bone.

* * * * *